United States Patent

Henning et al.

Patent Number: 5,807,274
Date of Patent: Sep. 15, 1998

[54] PUMP FOR USE IN NON-INVASIVE OR MINIMALLY INVASIVE DETECTION OF ANALYTES

[75] Inventors: Timothy P. Henning, Vernon Hills; Eric B. Shain, Glencoe; Tuan A. Elstrom, Lake Bluff; Kevin C. Warnke, Grayslake, all of Ill.

[73] Assignee: Abbott Laboratories, Abbott Park, Ill.

[21] Appl. No.: 890,762

[22] Filed: Jul. 11, 1997

Related U.S. Application Data

[63] Continuation of Ser. No. 573,805, Dec. 18, 1995, abandoned.

[51] Int. Cl.$^6$ .................................................. A61B 10/00
[52] U.S. Cl. ........................ 600/565; 600/573; 604/316
[58] Field of Search .................................. 604/313, 316; 600/562, 565, 573

[56] References Cited

U.S. PATENT DOCUMENTS 5,161,532  11/1992  Joseph .
5,383,290  1/1995   Grim .
5,549,584  8/1996   Gross .................................... 604/313

FOREIGN PATENT DOCUMENTS 0453283  10/1991  European Pat. Off. .
0513789  11/1992  European Pat. Off. .
0595237   5/1994  European Pat. Off. .

*Primary Examiner*—Max Hindenburg
*Assistant Examiner*—Pamela L. Wingood
*Attorney, Agent, or Firm*—David L. Weinstein; Gregory W. Steele

[57] ABSTRACT

This disclosure relates to a device and method for the non-invasive or minimally invasive withdrawal of fluids from a patient by the use of a self-actuated pump connected to a analyte sensing unit. The self-actuated pump is preferably mounted in the patient's shoe.

4 Claims, 5 Drawing Sheets

PUMP FOR USE IN NON-INVASIVE OR MINIMALLY INVASIVE DETECTION OF ANALYTES

This application is a continuation of application Ser. No. 08/573,805, filed Dec. 18, 1995, now abandoned.

FIELD OF THE INVENTION

This disclosure relates to a pump used for the non-invasive or minimally invasive withdrawal of fluids from a patient.

BACKGROUND OF THE INVENTION

The ability to accurately measure analytes in the blood, particularly glucose, is important in the management of diseases such as diabetes. Blood glucose levels must be maintained within a narrow range (about 3.5–6.5 mM). Glucose levels lower than this range (hypoglycemia) may lead to mental confusion, coma, or death. High glucose levels (hyperglycemia) cause excessive thirst and frequent urination. Sustained hyperglycemia has been linked to several of the complications of diabetes, such as kidney damage, neural damage, and blindness.

Blood glucose is maintained in many diabetics with routine injections of insulin. Unlike the normal functioning of the body's glucose control systems, injections of insulin incorporate no feedback mechanisms. Controlling glucose levels therefore requires continuous or frequent measurements of blood glucose concentration in order to determine the proper amount and frequency of insulin injections.

Conventional glucose measurement techniques require lancing of a convenient part of the body (normally a fingertip) with a lancet, milking the finger to produce a drop of blood at the impalement site, and depositing the drop of blood on a measurement device (such as an analysis strip). This lancing of the finger, at typical measurement frequencies of two to four times a day, is both painful and messy for the patient. The pain and inconvenience has additional and more serious implications of noncompliance, in that many patients will not maintain the recommended regimen of blood glucose measurement and thereby run the risk of improper glucose levels and consequent harmful effects.

In short, the inherent limitations of conventional blood glucose measurement techniques mean that patients either suffer this pain and inconvenience or neglect glucose monitoring and suffer the adverse physiological effects of improper glucose control. There is a clear need for a glucose measurement technique that minimizes or eliminates pain and inconvenience to the patient.

Several devices have been developed which use a pump to draw body fluid from the patient to a glucose detector or other analytical instrument. For example, U.S. Pat. No. 5,161,532 discloses the use of a pump to draw interstitial fluid from the skin to an integral glucose sensor. This system requires a pump capable of creating suction at a level of about 200–400 mmHg. European Patent Publication 0 595 237 discloses an analytical device for measuring blood constituents such as glucose, which also requires a suction pump capable of creating suction at a level of about 400 mmHg. The sampling of body fluid through the skin with a suction pump is also disclosed in European Patent Publication 0 513 789.

All of the above inventions require the use of a suction pump to effect fluid motion through the skin. While glucose monitoring via fluid extraction through the skin holds great promise, it is impractical if it requires the patient to use a bulky vacuum pump or power source as is suggested in the art. There is a clear need, therefore, for a vacuum source that is compact and does not require an external power source, which is suitable for use in a minimally invasive or non-invasive manner, thus allowing glucose monitoring to occur with minimum inconvenience to the patient.

SUMMARY OF THE INVENTION

The present disclosure provides a device for extracting and monitoring bodily fluids which comprises a self-actuated pump, a sensing unit, and pneumatic conduit connecting the self-actuated pump to the sensing unit. Preferably, the self-actuated pump is operated by walking. Most preferably, the pump is mounted in the patient's shoe.

Also provided is a method of extracting and monitoring an analyte in bodily fluids, by providing an extraction and monitoring device comprising the device previously described, activating the self-actuated pump and extracting the body fluid such that the fluid is in contact with the sensing unit, and detecting the presence or amount of the analyte in the body fluid with the sensing unit.

Additional, optional, features of the device and method provide a visual readout of the presence or amount of the analyte in the body fluid.

DETAILED DESCRIPTION OF PREFERRED EMBODIMENTS

Figure 1:
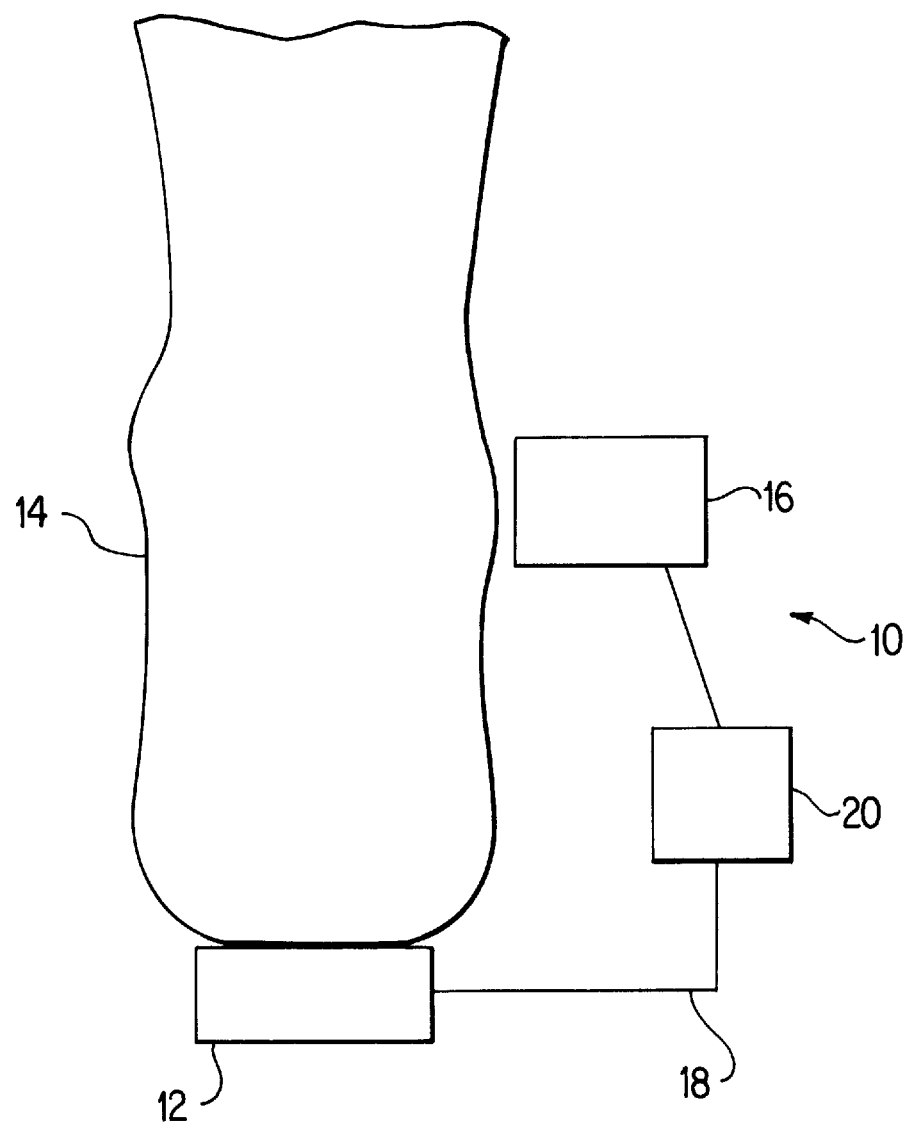
FIG. 1 shows the primary components of the device of the invention.

FIG. 1 shows the primary components of the device of the invention. The pneumatic assembly 10 includes a self-actuated pump 12 that is located adjacent a moving body part 14. As used in herein, "self-actuated" refers to a pump wherein the negative pressure produced by the by the pump is created by mechanical forces generated by an action of the patient's body, e.g., the forces created by walking, by action of the diaphragm, by movements of the arm, etc. The self-actuated pump 12 is pneumatically connected to a sensing unit 16 by pneumatic conduit 18. The sensing unit 16 is also located adjacent to the subject's body 14, preferably in a location near the location of the self-actuated pump 12. In some embodiments, a control unit 20 is located between and is pneumatically connected to the self-actuated pump 12 and the sensing unit 16.

The component or analyte of interest which can be measured with the use of the device and/or method of the invention is not important for the operation or usefulness of the invention. Thus any component of interest which is found in a body fluid and is suitable for extraction through the skin can be measured as disclosed herein. Examples of analytes or biological components of interest are known and include such well known analytes of clinical significance as glucose, hemoglobin, lipids, cholesterol, protein, etc. Other analytes will be readily apparent to those skilled in the art.

EXAMPLE 1

Figure 2A:
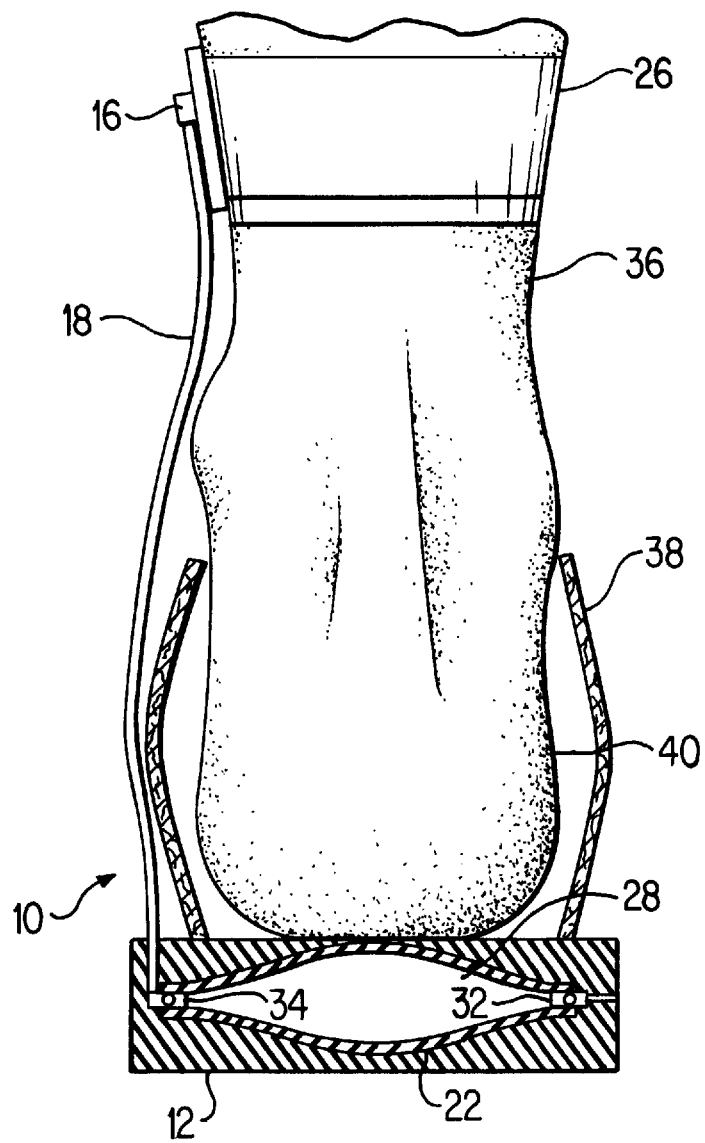
FIGS. 2a and 2b show two alternate embodiments of the invention.
Figure 2B:
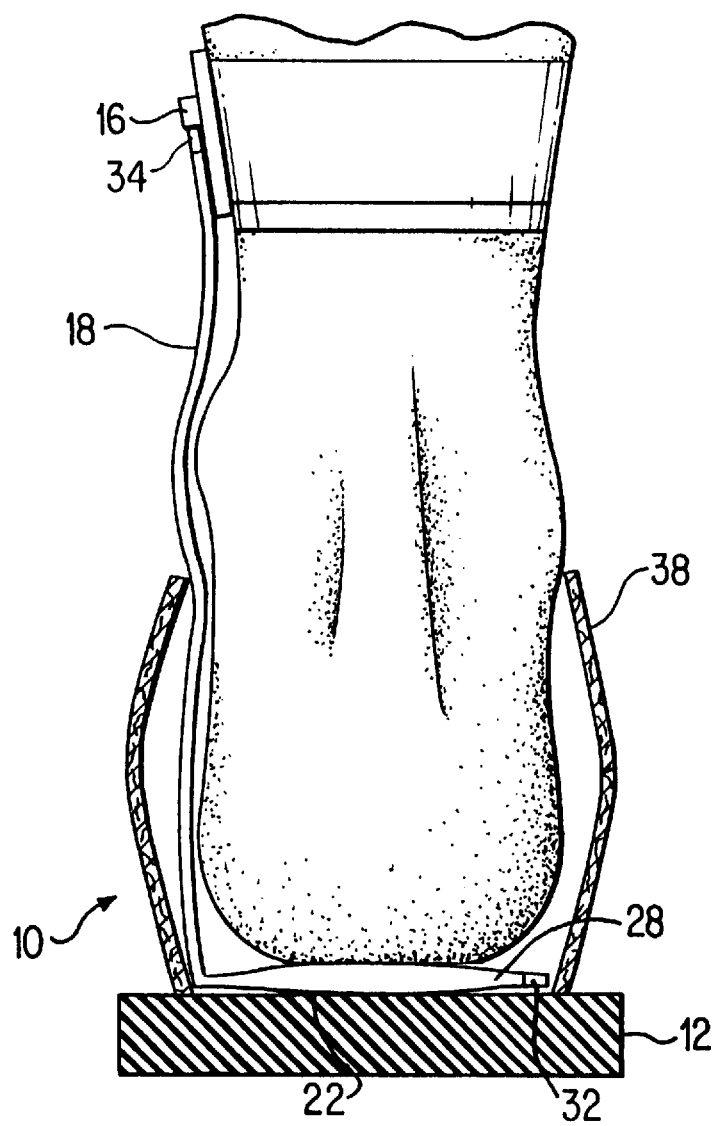

A more detailed illustration of two embodiments of the invention are shown in FIGS. 2a and 2b. The self-actuated pump 12 is located either within the shoe (FIG. 2a) or in an insert (FIG. 2B), and is operated by the downward force exerted by the subject's foot 40 during normal walking. In both embodiments, the sensing unit 16 is fastened to the subject's leg 26.

In the embodiment shown in FIG. 2a, the device of the invention is partially housed inside a shoe 38. The pneumatic assembly comprises a self-actuated pump 12, located inside shoe 38 in the region directly below the heel of the subject's foot 40. The self-actuated pump 12 includes a diaphragm 22, two check valves 32 and 34, and a cavity 28. The first check valve 34, oriented to allow the passage of gas or fluid into the cavity 28, is connected via pneumatic conduit 18 to the sensing unit 16, which is attached to the subject's leg 36 by means of a fastening means 26. In this embodiment, the fastening means is shown as a cuff. A second check valve 32 is oriented to allow the passage of gas or fluid out of the cavity 28.

In operation of this embodiment, the mechanical motion of the subject's body, in this case the force applied by the subject's foot 40 while walking, provides mechanical power to the self-actuated pump 12. The downward force applied by the heel 40 inwardly deflects the diaphragm 22 compressing the cavity 28, and thereby causing a portion of the gas contained in the cavity to be expelled via the second check valve 32. When the downward force of the foot 40 is removed (for example, when the subject lifts that foot 40 as part of his normal gait), the restorative force of the diaphragm 22 causes the cavity 28 to return to its previous volume. This restoration of the volume of the cavity 28 creates a region of relatively reduced pressure within the cavity 28, which is pneumatically linked via the first check valve 34 and the pneumatic conduit 18 to the sensing unit 16. A region of relatively reduced pressure is thus created within the sensing unit 16, which may be used to effect the exudation of bodily fluid from the leg 36 for sampling and analysis.

An alternate design is shown in FIG. 2b and shows the self-actuated pump 12 housed as an insert which can be placed within the subject's shoe 38. In this embodiment, the second check valve 34 is located adjacent the sensing unit 16; but otherwise the operation of the device is as described above.

A variety of designs exist for sensing units 16. For example, sensing units are described in U.S. Pat. No. 5,161,532 and European Patent Publications 0 513 789 and 0 595 237. These devices are all similar in that they require a means of creating a relatively reduced pressure, for example an absolute pressure of about 400 mmHg. The restorative force of the diaphragm 22 is sufficient to create a region of this pressure within the cavity 28, which is transmitted to the sensing unit 16 to enable the analysis of the desired components of the bodily fluid to occur.

Figure 3:
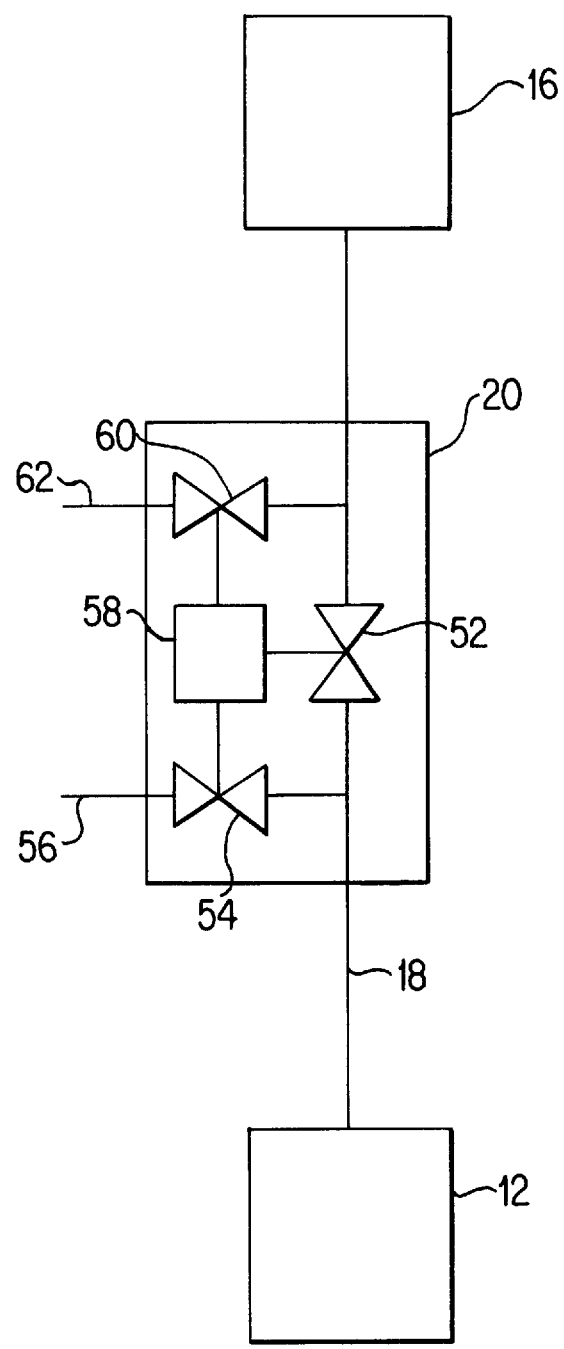
FIG. 3 shows a preferred embodiment employing a control unit.

A preferred embodiment employs a control unit as shown in FIG. 3. In this example an electrically operated valve 52 controls the transmission of the relatively reduced pressure from the self-actuated pump 12 to the sensing unit 16. A vent valve 54 is connected to the pneumatic conduit 18 at a location between the self-actuated pump 12 and the control valve 52. The vent valve is pneumatically connected to ambient atmosphere via a vent line 56. A second vent valve 60 may be connected to the pneumatic conduit 18 at a location between the sensing unit 16 and the control valve 52 and which is pneumatically connected to ambient atmosphere via a second vent line 62. An electronic control system 58 controls the operation of the control valve 52 and the vent valves 54 and 60. When analysis of the bodily fluid is desired (as determined by a time signal from a clock, a manually applied signal from the subject, or other signal), the control system 58 causes the control valve 52 to be open and the vent valves 54 and 60 to be closed. In this state, the relatively reduced pressure created by the self-actuated pump 12 is transmitted to the sensing unit 16 where the fluid extraction and analysis may occur. In order to avoid unnecessary application of this suction pressure, when the analysis is completed the control system 58 closes control valve 52 to shut and opens vent valves 54 and 60. In this mode air enters the pneumatic conduit 18 via vent valve 60, dissipating the relatively reduced pressure in the sensing unit 16 and improving the comfort of the subject. The vent valve 54 is open, allowing the self-actuated pump 12 to continue to operate, taking air in via the vent line 56 and the vent valve 54 in lieu of creating a region of relatively reduced pressure in the cavity of self-actuated pump 12.

EXAMPLE 2—BELT PUMP

Figure 4:
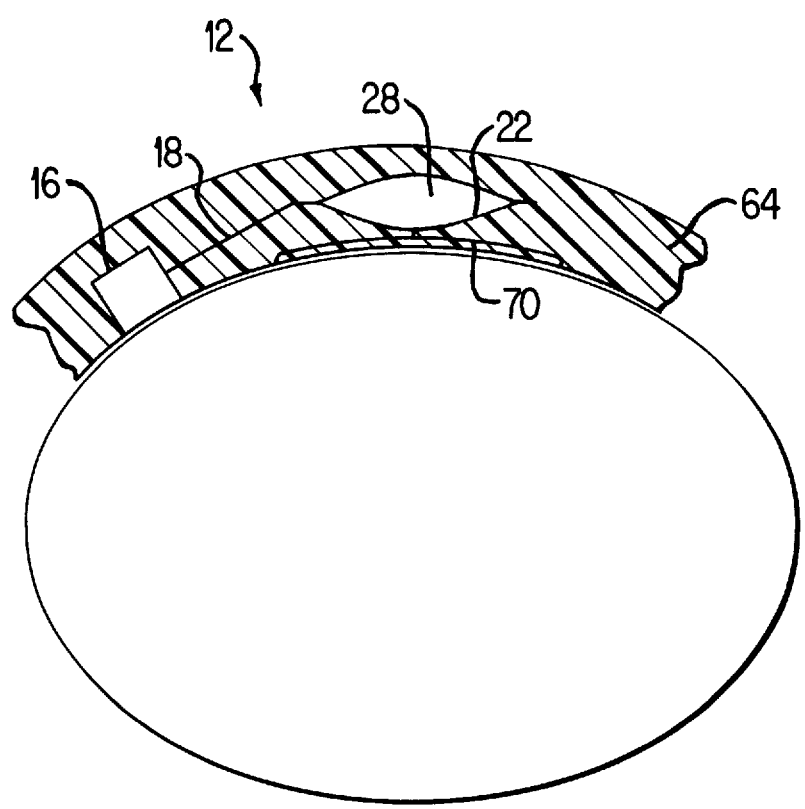
FIG. 4 shows a further embodiment of the invention.

A second example of an embodiment of the invention is illustrated in FIG. 4. The self-actuated pump 12 is located within a belt 64 which is fastened around the subject's waist. In this embodiment, the mechanical motion of the subject's breathing is used to transmit power to the self-actuated pump 12. Here, a relatively large portion of the patient's body surface area is linked via a mechanical linkage 70 to a relatively small diaphragm 22 in order to apply sufficient force to create the required reduction in pressure of the cavity 28. In this case the sensing unit 16 may be placed against the patient's waist, thorax or other, more remote, body sites. Note that other articles of clothing which surround the subject's waist or thorax (e.g., trousers, brassieres, briefs, etc.) may be modified to incorporate similar embodiments therein.

The present invention has been described with reference to preferred embodiments. One of skill in the art will readily appreciate that changes, alterations or modifications can be made to these embodiments without departing from the true scope and spirit of the invention.

We claim:

1. A device for extracting and monitoring a bodily fluid of a patient, comprising:
   (a) a self-actuated pump located adjacent a moving body part of said patient, said pump capable of producing a negative pressure by mechanical forces generated by said moving body part to extract said bodily fluid;
   (b) a sensing unit located adjacent to said patient's body, and
   (c) pneumatic conduit connecting the self-actuated pump to the sensing unit,
   wherein the self-actuated pump is operated by walking.

2. A device for extracting and monitoring a bodily fluid of a patient, comprising:
   (a) a self-actuated pump located adjacent a moving body part of said patient, said pump capable of producing a negative pressure by mechanical forces generated by said moving body part to extract said bodily fluid,
   (b) a sensing unit located adjacent to said patient's body, and
   (c) a pneumatic conduit connecting the self-actuated pump to the sensing unit,
   wherein the self-actuated pump is operated by motion caused by breathing of the patient.

3. A method of extracting and monitoring an analyte in a bodily fluid of a patient comprising the steps of:

(a) providing an extraction and monitoring device comprising
  (i) a self-actuated pump located adjacent a moving body part of said patient, said pump capable of producing a negative pressure by mechanical forces generated by said moving body part to extract said bodily fluid, wherein said mechanical forces are generated by an up and down motion of said body part or by a motion caused by breathing of the patient,
  (ii) a sensing unit located adjacent to said patient's body, and
  (iii) a pneumatic conduit connecting the self-actuated pump to the sensing unit;
(b) activating the self-actuated pump and extracting the bodily fluid such that the fluid is in contact with the sensing unit; and
(c) detecting presence or amount of the analyte in the bodily fluid with the sensing unit.

4. The method according to claim 3 further providing a visual readout of the presence or amount of the analyte in the body fluid.

* * * * *